United States Patent [19]

Izu et al.

[11] Patent Number: 5,795,765

[45] Date of Patent: Aug. 18, 1998

[54] GENE ENCODING ENDOGLYCOCERAMIDASE

[75] Inventors: Hiroyuki Izu; Yoko Kurome, both of Kusatsu; Yoshiya Izumi, Onojyo; Mutsumi Sano, Otsu; Ikunoshin Kato, Uji; Makoto Ito, Fukuoka, all of Japan

[73] Assignee: Takara Shuzo Co., Ltd., Kyoto-Fu, Japan

[21] Appl. No.: 672,571

[22] Filed: Jun. 28, 1996

[30] Foreign Application Priority Data

Jun. 29, 1995 [JP] Japan .................... 7-188465

[51] Int. Cl.$^6$ .................. C12N 9/24; C12N 15/00; C12N 5/00; C12N 1/20
[52] U.S. Cl. .................. 435/200; 435/320.1; 435/240.2; 435/252.3; 536/23.2
[58] Field of Search .................. 435/200, 320.1, 435/240.2, 252.3; 536/23.2

[56] References Cited

FOREIGN PATENT DOCUMENTS 62-122587  6/1987  Japan .

OTHER PUBLICATIONS

Makoto Ito et al., The Journal of Biological Chemistry, A Novel Glycosphingolipid degrading . . . , vol. 261, pp. 14278–14282, 1986.

Makoto Ito et al., The Journal of Biological Chemistry, Purification and Characterization . . . , vol. 264, pp. 9510–9519, 1989.

Su–Chen Li et al., Biochemical and Biophysical Research Communications, A Unique Glycosphinolipid . . . , vol. 141, pp. 346–352, 1986.

Hisashi Ashida et al., European Journal of Biochemistry, Purification and Characterization . . . , vol. 205, pp. 729–735, 1992.

The FASEB Journal, vol. 8, A1439, 1994.

Makoto Ito et al., The Journal of Biological Chemistry, Activatior Proteins . . . , vol. 266(12), pp. 7919–1926, 1991.

J. Rudinger (1976) Characteristics of the amino acids as Components of a peptide hormone sequence, In: Peptide Hormones, Ed. J. A. Parsons, 2–7, Jun. 1976.

*Primary Examiner*—Robert A. Wax
*Assistant Examiner*—Einar Stole

[57] ABSTRACT

An isolated DNA having a sequence encoding a polypeptide possessing endoglycoceramidase activity or functionally equivalent variants thereof, and a method for producing a polypeptide possessing endoglycoceramidase activity or functionally equivalent variants thereof by gene recombinant technology.

9 Claims, 4 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 490 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Met  Arg  Arg  Thr  Arg  Leu  Val  Ser  Leu  Ile  Val  Thr  Gly  Ser  Leu
 1                  5                        10                       15

Val  Phe  Gly  Gly  Gly  Val  Ala  Ala  Ala  Gln  Ser  Ser  Leu  Ala  Ala
                    20                       25                       30

Ser  Gly  Ser  Gly  Ser  Gly  Ser  Gly  Thr  Ala  Leu  Thr  Pro  Ser  Tyr
                    35                       40                       45

Leu  Lys  Asp  Asp  Asp  Gly  Arg  Ser  Leu  Ile  Leu  Arg  Gly  Phe  Asn
                    50                       55                       60

Thr  Ala  Ser  Ser  Ala  Lys  Ser  Ala  Pro  Asp  Gly  Met  Pro  Gln  Phe
                    65                       70                       75

Thr  Glu  Ala  Asp  Leu  Ala  Arg  Glu  Tyr  Ala  Asp  Met  Gly  Thr  Asn
                    80                       85                       90

Phe  Val  Arg  Phe  Leu  Ile  Ser  Trp  Arg  Ser  Val  Glu  Pro  Ala  Pro
                    95                       100                      105

Gly  Val  Tyr  Asp  Gln  Gln  Tyr  Leu  Asp  Arg  Val  Glu  Asp  Arg  Val
                    110                      115                      120

Gly  Trp  Tyr  Ala  Glu  Arg  Gly  Tyr  Lys  Val  Met  Leu  Asp  Met  His
                    125                      130                      135

Gln  Asp  Val  Tyr  Ser  Gly  Ala  Ile  Thr  Pro  Glu  Gly  Asn  Ser  Gly
                    140                      145                      150
```

-continued

| | | | | | | | | | | | | | | |
|---|---|---|---|---|---|---|---|---|---|---|---|---|---|---|
| Asn | Gly | Ala | Gly | Ala 155 | Ile | Gly | Asn | Gly | Ala 160 | Pro | Ala | Trp | Ala | Thr 165 |
| Tyr | Met | Asp | Gly | Leu 170 | Pro | Val | Glu | Pro | Gln 175 | Pro | Arg | Trp | Glu | Leu 180 |
| Tyr | Tyr | Ile | Gln | Pro 185 | Gly | Val | Met | Arg | Ala 190 | Phe | Asp | Asn | Phe | Trp 195 |
| Asn | Thr | Thr | Gly | Lys 200 | His | Pro | Glu | Leu | Val 205 | Glu | His | Tyr | Ala | Lys 210 |
| Ala | Trp | Arg | Ala | Val 215 | Ala | Asp | Arg | Phe | Ala 220 | Asp | Asn | Asp | Ala | Val 225 |
| Val | Ala | Tyr | Asp | Leu 230 | Met | Asn | Glu | Pro | Phe 235 | Gly | Gly | Ser | Leu | Gln 240 |
| Gly | Pro | Ala | Phe | Glu 245 | Ala | Gly | Pro | Leu | Ala 250 | Ala | Met | Tyr | Gln | Arg 255 |
| Thr | Thr | Asp | Ala | Ile 260 | Arg | Gln | Val | Asp | Gln 265 | Asp | Thr | Trp | Val | Cys 270 |
| Val | Ala | Pro | Gln | Ala 275 | Ile | Gly | Val | Asn | Gln 280 | Gly | Leu | Pro | Ser | Gly 285 |
| Leu | Thr | Lys | Ile | Asp 290 | Asp | Pro | Arg | Ala | Gly 295 | Gln | Gln | Arg | Ile | Ala 300 |
| Tyr | Cys | Pro | His | Leu 305 | Tyr | Pro | Leu | Pro | Leu 310 | Asp | Ile | Gly | Asp | Gly 315 |
| His | Glu | Gly | Leu | Ala 320 | Arg | Thr | Leu | Thr | Asp 325 | Val | Thr | Ile | Asp | Ala 330 |
| Trp | Arg | Ala | Asn | Thr 335 | Ala | His | Thr | Ala | Arg 340 | Val | Leu | Gly | Asp | Val 345 |
| Pro | Ile | Ile | Leu | Gly 350 | Glu | Phe | Gly | Leu | Asp 355 | Thr | Thr | Leu | Pro | Gly 360 |
| Ala | Arg | Asp | Tyr | Ile 365 | Glu | Arg | Val | Tyr | Gly 370 | Thr | Ala | Arg | Glu | Met 375 |
| Gly | Ala | Gly | Val | Ser 380 | Tyr | Trp | Ser | Ser | Asp 385 | Pro | Gly | Pro | Trp | Gly 390 |
| Pro | Tyr | Leu | Pro | Asp 395 | Gly | Thr | Gln | Thr | Leu 400 | Leu | Val | Asp | Thr | Leu 405 |
| Asn | Lys | Pro | Tyr | Pro 410 | Arg | Ala | Val | Ala | Gly 415 | Thr | Pro | Thr | Glu | Trp 420 |
| Ser | Ser | Thr | Ser | Asp 425 | Arg | Leu | Gln | Leu | Thr 430 | Ile | Glu | Pro | Asp | Ala 435 |
| Ala | Ile | Thr | Ala | Pro 440 | Thr | Glu | Ile | Tyr | Leu 445 | Pro | Glu | Ala | Gly | Phe 450 |
| Pro | Gly | Asp | Val | His 455 | Val | Glu | Gly | Ala | Asp 460 | Val | Val | Gly | Trp | Asp 465 |
| Arg | Gln | Ser | Arg | Leu 470 | Leu | Thr | Val | Arg | Thr 475 | Pro | Ala | Asp | Ser | Gly 480 |
| Asn | Val | Thr | Val | Thr 485 | Val | Thr | Pro | Ala | Ala 490 | | | | | |

( 2 ) INFORMATION FOR SEQ ID NO:2:

( i ) SEQUENCE CHARACTERISTICS:
        ( A ) LENGTH: 1473 base pairs
        ( B ) TYPE: nucleic acid
        ( C ) STRANDEDNESS: double
        ( D ) TOPOLOGY: linear     ( i i ) MOLECULE TYPE: genomic DNA ( x i ) SEQUENCE DESCRIPTION: SEQ ID NO:2:

| | | | | | |
|---|---|---|---|---|---|
| GTGCGTCGCA | CCCGGCTCGT | ATCGCTGATC | GTGACAGGTT | CGCTGGTGTT | CGGCGGCGGC | 60
| GTTGCCGCCG | CTCAGAGCAG | CTTGGCCGCA | TCCGGAAGCG | GAAGTGGCAG | TGGTACCGCG | 120
| CTGACGCCGT | CCTACCTGAA | GGACGATGAC | GGCCGCTCAC | TGATCCTGCG | CGGGTTCAAC | 180
| ACGGCATCGA | GCGCGAAGAG | CGCGCCGGAC | GGCATGCCGC | AGTTCACCGA | GGCGGACCTG | 240
| GCGCGCGAGT | ATGCAGACAT | GGGAACCAAC | TTCGTTCGGT | TCCTCATCTC | GTGGCGGTCG | 300
| GTCGAACCAG | CACCGGGCGT | GTACGACCAG | CAGTATCTGG | ACCGTGTCGA | AGATCGGGTC | 360
| GGCTGGTACG | CCGAGCGCGG | CTACAAGGTG | ATGCTCGACA | TGCACCAGGA | CGTGTACTCC | 420
| GGCGCGATCA | CCCCGGAGGG | CAACAGCGGC | AACGGTGCCG | CGCCATCGG | CAACGGCGCA | 480
| CCGGCCTGGG | CGACCTACAT | GGACGGCCTT | CCGGTCGAGC | CGCAGCCCCG | GTGGGAGCTG | 540
| TACTACATCC | AGCCCGGCGT | GATGCGCGCG | TTCGACAACT | TCTGGAACAC | CACCGGCAAG | 600
| CACCCCGAAC | TCGTCGAGCA | CTACGCGAAA | GCGTGGCGGG | CGGTCGCCGA | CCGATTCGCC | 660
| GACAACGACG | CCGTCGTGGC | CTACGACCTG | ATGAACGAGC | CGTTCGGAGG | ATCCCTGCAG | 720
| GGACCGGCGT | TCGAGGCAGG | GCCGCTCGCC | GCGATGTACC | AGCGCACCAC | CGACGCCATC | 780
| CGGCAGGTAG | ACCAGGACAC | CTGGGTCTGC | GTGGCCCCGC | AGGCGATCGG | CGTCAACCAG | 840
| GGTCTCCCCA | GCGGGCTCAC | CAAGATCGAC | GACCCTCGTG | CGGGTCAACA | GCGCATCGCG | 900
| TACTGCCCGC | ACCTCTACCC | ACTGCCGCTG | GATATCGGTG | ACGGCCACGA | GGGCCTGGCC | 960
| CGGACGCTCA | CCGACGTGAC | CATCGACGCC | TGGCGTGCCA | ACACCGCCCA | CACCGCCCGT | 1020
| GTGCTGGGTG | ACGTGCCCAT | CATCCTCGGC | GAGTTCGGCC | TGGACACAAC | GCTGCCCGGG | 1080
| GCCCGGGATT | ACATCGAACG | CGTCTACGGG | ACCGCGCGAG | AGATGGGGGC | CGGAGTCTCG | 1140
| TACTGGTCCA | GCGATCCCGG | CCCCTGGGGC | CCGTACCTGC | CTGACGGCAC | GCAGACGCTG | 1200
| CTCGTCGACA | CCCTGAACAA | GCCGTACCCC | CGCGCAGTGG | CCGGCACACC | CACCGAGTGG | 1260
| TCGTCGACCT | CCGATCGCCT | CCAATTGACG | ATCGAGCCGG | ACGCCGCGAT | CACCGCTCCC | 1320
| ACCGAGATCT | ACCTCCCGGA | GGCAGGATTC | CCGGGCGACG | TCCACGTCGA | AGGCGCCGAC | 1380
| GTCGTGGGGT | GGGATCGGCA | GAGTCGACTG | CTCACGGTGC | GCACTCCGGC | CGACTCGGGC | 1440
| AACGTGACCG | TGACGGTCAC | TCCGGCAGCC | TGA | | | 1473

( 2 ) INFORMATION FOR SEQ ID NO:3:

( i ) SEQUENCE CHARACTERISTICS:
        ( A ) LENGTH: 461 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

| Ala | Ser | Gly | Ser | Gly | Ser | Gly | Thr | Ala | Leu | Thr | Pro | Ser |
|---|---|---|---|---|---|---|---|---|---|---|---|---|
| 1 | | | | 5 | | | | 10 | | | | 15 |

| Tyr | Leu | Lys | Asp | Asp | Gly | Arg | Ser | Leu | Ile | Leu | Arg | Gly | Phe |
|---|---|---|---|---|---|---|---|---|---|---|---|---|---|
| | | | | 20 | | | | 25 | | | | | 30 |

| Asn | Thr | Ala | Ser | Ser | Ala | Lys | Ser | Ala | Pro | Asp | Gly | Met | Pro | Gln |
|---|---|---|---|---|---|---|---|---|---|---|---|---|---|---|
| | | | | 35 | | | | | 40 | | | | | 45 |

| Phe | Thr | Glu | Ala | Asp | Leu | Ala | Arg | Glu | Tyr | Ala | Asp | Met | Gly | Thr |
|---|---|---|---|---|---|---|---|---|---|---|---|---|---|---|
| | | | | 50 | | | | | 55 | | | | | 60 |

| Asn | Phe | Val | Arg | Phe | Leu | Ile | Ser | Trp | Arg | Ser | Val | Glu | Pro | Ala |
|---|---|---|---|---|---|---|---|---|---|---|---|---|---|---|
| | | | | 65 | | | | | 70 | | | | | 75 |

-continued

| | | | | | | | | | | | | | | |
|---|---|---|---|---|---|---|---|---|---|---|---|---|---|---|
| Pro | Gly | Val | Tyr | Asp<br>80 | Gln | Gln | Tyr | Leu | Asp<br>85 | Arg | Val | Glu | Asp | Arg<br>90 |
| Val | Gly | Trp | Tyr | Ala<br>95 | Glu | Arg | Gly | Tyr | Lys<br>100 | Val | Met | Leu | Asp | Met<br>105 |
| His | Gln | Asp | Val | Tyr<br>110 | Ser | Gly | Ala | Ile | Thr<br>115 | Pro | Glu | Gly | Asn | Ser<br>120 |
| Gly | Asn | Gly | Ala | Gly<br>125 | Ala | Ile | Gly | Asn | Gly<br>130 | Ala | Pro | Ala | Trp | Ala<br>135 |
| Thr | Tyr | Met | Asp | Gly<br>140 | Leu | Pro | Val | Glu | Pro<br>145 | Gln | Pro | Arg | Trp | Glu<br>150 |
| Leu | Tyr | Tyr | Ile | Gln<br>155 | Pro | Gly | Val | Met | Arg<br>160 | Ala | Phe | Asp | Asn | Phe<br>165 |
| Trp | Asn | Thr | Thr | Gly<br>170 | Lys | His | Pro | Glu | Leu<br>175 | Val | Glu | His | Tyr | Ala<br>180 |
| Lys | Ala | Trp | Arg | Ala<br>185 | Val | Ala | Asp | Arg | Phe<br>190 | Ala | Asp | Asn | Asp | Ala<br>195 |
| Val | Val | Ala | Tyr | Asp<br>200 | Leu | Met | Asn | Glu | Pro<br>205 | Phe | Gly | Gly | Ser | Leu<br>210 |
| Gln | Gly | Pro | Ala | Phe<br>215 | Glu | Ala | Gly | Pro | Leu<br>220 | Ala | Ala | Met | Tyr | Gln<br>225 |
| Arg | Thr | Thr | Asp | Ala<br>230 | Ile | Arg | Gln | Val | Asp<br>235 | Gln | Asp | Thr | Trp | Val<br>240 |
| Cys | Val | Ala | Pro | Gln<br>245 | Ala | Ile | Gly | Val | Asn<br>250 | Gln | Gly | Leu | Pro | Ser<br>255 |
| Gly | Leu | Thr | Lys | Ile<br>260 | Asp | Asp | Pro | Arg | Ala<br>265 | Gly | Gln | Gln | Arg | Ile<br>270 |
| Ala | Tyr | Cys | Pro | His<br>275 | Leu | Tyr | Pro | Leu | Pro<br>280 | Leu | Asp | Ile | Gly | Asp<br>285 |
| Gly | His | Glu | Gly | Leu<br>290 | Ala | Arg | Thr | Leu | Thr<br>295 | Asp | Val | Thr | Ile | Asp<br>300 |
| Ala | Trp | Arg | Ala | Asn<br>305 | Thr | Ala | His | Thr | Ala<br>310 | Arg | Val | Leu | Gly | Asp<br>315 |
| Val | Pro | Ile | Ile | Leu<br>320 | Gly | Glu | Phe | Gly | Leu<br>325 | Asp | Thr | Thr | Leu | Pro<br>330 |
| Gly | Ala | Arg | Asp | Tyr<br>335 | Ile | Glu | Arg | Val | Tyr<br>340 | Gly | Thr | Ala | Arg | Glu<br>345 |
| Met | Gly | Ala | Gly | Val<br>350 | Ser | Tyr | Trp | Ser | Ser<br>355 | Asp | Pro | Gly | Pro | Trp<br>360 |
| Gly | Pro | Tyr | Leu | Pro<br>365 | Asp | Gly | Thr | Gln | Thr<br>370 | Leu | Leu | Val | Asp | Thr<br>375 |
| Leu | Asn | Lys | Pro | Tyr<br>380 | Pro | Arg | Ala | Val | Ala<br>385 | Gly | Thr | Pro | Thr | Glu<br>390 |
| Trp | Ser | Ser | Thr | Ser<br>395 | Asp | Arg | Leu | Gln | Leu<br>400 | Thr | Ile | Glu | Pro | Asp<br>405 |
| Ala | Ala | Ile | Thr | Ala<br>410 | Pro | Thr | Glu | Ile | Tyr<br>415 | Leu | Pro | Glu | Ala | Gly<br>420 |
| Phe | Pro | Gly | Asp | Val<br>425 | His | Val | Glu | Gly | Ala<br>430 | Asp | Val | Val | Gly | Trp<br>435 |
| Asp | Arg | Gln | Ser | Arg<br>440 | Leu | Leu | Thr | Val | Arg<br>445 | Thr | Pro | Ala | Asp | Ser<br>450 |
| Gly | Asn | Val | Thr | Val<br>455 | Thr | Val | Thr | Pro | Ala<br>460 | Ala | | | | |

( 2 ) INFORMATION FOR SEQ ID NO:4:

( i ) SEQUENCE CHARACTERISTICS:
    ( A ) LENGTH: 1386 base pairs
    ( B ) TYPE: nucleic acid
    ( C ) STRANDEDNESS: double
    ( D ) TOPOLOGY: linear ( i i ) MOLECULE TYPE: genomic DNA ( x i ) SEQUENCE DESCRIPTION: SEQ ID NO:4:

| | | | | | | |
|---|---|---|---|---|---|---|
| GCATCCGGAA | GCGGAAGTGG | CAGTGGTACC | GCGCTGACGC | CGTCCTACCT | GAAGGACGAT | 60 |
| GACGGCCGCT | CACTGATCCT | GCGCGGGTTC | AACACGGCAT | CGAGCGCGAA | GAGCGCGCCG | 120 |
| GACGGCATGC | CGCAGTTCAC | CGAGGCGGAC | CTGGCGCGCG | AGTATGCAGA | CATGGGAACC | 180 |
| AACTTCGTTC | GGTTCCTCAT | CTCGTGGCGG | TCGGTCGAAC | CAGCACCGGG | CGTGTACGAC | 240 |
| CAGCAGTATC | TGGACCGTGT | CGAAGATCGG | GTCGGCTGGT | ACGCCGAGCG | CGGCTACAAG | 300 |
| GTGATGCTCG | ACATGCACCA | GGACGTGTAC | TCCGGCGCGA | TCACCCCGGA | GGGCAACAGC | 360 |
| GGCAACGGTG | CCGGCGCCAT | CGGCAACGGC | GCACCGGCCT | GGGCGACCTA | CATGGACGGC | 420 |
| CTTCCGGTCG | AGCCGCAGCC | CCGGTGGGAG | CTGTACTACA | TCCAGCCCGG | CGTGATGCGC | 480 |
| GCGTTCGACA | ACTTCTGGAA | CACCACCGGC | AAGCACCCCG | AACTCGTCGA | GCACTACGCG | 540 |
| AAAGCGTGGC | GGGCGGTCGC | CGACCGATTC | GCCGACAACG | ACGCCGTCGT | GGCCTACGAC | 600 |
| CTGATGAACG | AGCCGTTCGG | AGGATCCCTG | CAGGGACCGG | CGTTCGAGGC | AGGGCCGCTC | 660 |
| GCCGCGATGT | ACCAGCGCAC | CACCGACGCC | ATCCGGCAGG | TAGACCAGGA | CACCTGGGTC | 720 |
| TGCGTGGCCC | CGCAGGCGAT | CGGCGTCAAC | CAGGGTCTCC | CCAGCGGGCT | CACCAAGATC | 780 |
| GACGACCCTC | GTGCGGGTCA | ACAGCGCATC | GCGTACTGCC | CGCACCTCTA | CCCACTGCCG | 840 |
| CTGGATATCG | GTGACGGCCA | CGAGGGCCTG | GCCCGGACGC | TCACCGACGT | GACCATCGAC | 900 |
| GCCTGGCGTG | CCAACACCGC | CCACACCGCC | CGTGTGCTGG | GTGACGTGCC | CATCATCCTC | 960 |
| GGCGAGTTCG | GCCTGGACAC | AACGCTGCCC | GGGGCCCGGG | ATTACATCGA | ACGCGTCTAC | 1020 |
| GGGACCGCGC | GAGAGATGGG | GGCCGGAGTC | TCGTACTGGT | CCAGCGATCC | CGGCCCCTGG | 1080 |
| GGCCCGTACC | TGCCTGACGG | CACGCAGACG | CTGCTCGTCG | ACACCCTGAA | CAAGCCGTAC | 1140 |
| CCCCGCGCAG | TGGCCGGCAC | ACCACCGAG | TGGTCGTCGA | CCTCCGATCG | CCTCCAATTG | 1200 |
| ACGATCGAGC | CGGACGCCGC | GATCACCGCT | CCCACCGAGA | TCTACCTCCC | GGAGGCAGGA | 1260 |
| TTCCCGGGCG | ACGTCCACGT | CGAAGGCGCC | GACGTCGTGG | GGTGGGATCG | GCAGAGTCGA | 1320 |
| CTGCTCACGG | TGCGCACTCC | GGCCGACTCG | GGCAACGTGA | CCGTGACGGT | CACTCCGGCA | 1380 |
| GCCTGA | | | | | | 1386 |

( 2 ) INFORMATION FOR SEQ ID NO:5:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear   ( i i ) MOLECULE TYPE: peptide   ( v ) FRAGMENT TYPE: internal fragment   ( x i ) SEQUENCE DESCRIPTION: SEQ ID NO:5:

```
Ser Ala Pro Asp Gly Met Pro Gln Phe Thr Glu Ala Asp Leu Ala
 1               5                  10                  15

Arg Glu Tyr Ala Asp Met Gly Thr Asn Phe
20                  25
```

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:6:

```
Ile  Asp  Asp  Pro  Arg  Ala  Gly  Gln  Gln  Arg  Ile  Ala  Tyr  Pro  Pro
 1                  5                        10                       15

His  Leu  Tyr  Pro  Leu  Pro  Leu  Asp  Ile  Gly
20                  25
```

( 2 ) INFORMATION FOR SEQ ID NO:7:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:7:

```
Ala  Trp  Arg  Ala  Val  Ala  Asp  Arg  Phe  Ala  Asp  Asn  Asp  Ala  Val
 1                  5                        10                       15

Val  Ala  Tyr  Xaa  Leu  Met  Asn  Glu  Pro  Phe  Gly  Gly  Ser  Leu  Gln
20                  25                       30

Gly
```

( 2 ) INFORMATION FOR SEQ ID NO:8:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:8:

```
Val  Met  Leu  Asp  Met  His  Gln  Asp  Val  Tyr  Ser  Gly  Ala  Ile  Thr
 1                  5                        10                       15

Pro  Glu  Gly  Asn  Ser  Gly  Asn  Gly  Ala  Gly  Ala  Ile  Gly  Asn  Gly
20                  25                       30
```

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:9:

```
Pro Tyr Pro Arg Ala Val Ala Gly Thr Pro Thr Glu Trp Ser Ser
 1               5                   10                  15

Thr Xaa Asp Arg Leu Gln
 20
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:10:

```
His Pro Glu Leu Val Glu His Tyr Ala Lys
 1               5                   10
```

( 2 ) INFORMATION FOR SEQ ID NO:11:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:11:

```
Asp Asp Asp Gly Arg Ser Leu Ile Leu Arg Gly Phe Asn Thr Ala
 1               5                   10                  15

Ser Ser Ala Lys
```

( 2 ) INFORMATION FOR SEQ ID NO:12:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:12:

```
AAGTCSGCCC CCGACGGYAT GCCSCAGTTC ACSGARGCCG ACCTCGC                    47
```

( 2 ) INFORMATION FOR SEQ ID NO:13:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:13:

```
TTCACCGAGG CCGACCTSGC SCGSGARTAY GCCGACATGG GYACCAACTT                 50
```

( 2 ) INFORMATION FOR SEQ ID NO:14:

( i ) SEQUENCE CHARACTERISTICS:
        ( A ) LENGTH: 6 amino acids
        ( B ) TYPE: amino acid ( C ) STRANDEDNESS: single
            ( D ) TOPOLOGY: linear ( i i ) MOLECULE TYPE: peptide ( x i ) SEQUENCE DESCRIPTION: SEQ ID NO:14:

Met  Ala  Met  Ile  Thr  Asn
 1                      5

( 2 ) INFORMATION FOR SEQ ID NO:15:

( i ) SEQUENCE CHARACTERISTICS:
            ( A ) LENGTH: 18 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:15:

Met  Ala  Met  Ile  Thr  Asn  Ser  Ser  Ser  Val  Pro  Glu  Asp  Pro  Leu
 1                      5                          10                         15
Glu  Ser  Thr

GENE ENCODING ENDOGLYCOCERAMIDASE

BACKGROUND OF THE INVENTION

1. Field of the Invention

The present invention relates to a DNA encoding a polypeptide possessing endoglycoceramidase activity. Specifically, the present invention relates to a nucleotide sequence encoding endoglycoceramidase, an enzyme useful for structural, functional and other analyses of glycolipids in sugar chain engineering, and to an amino acid sequence thereof. The present invention also relates to an industrial production method for a polypeptide possessing endoglycoceramidase activity.

2. Discussion of the Related Art

In a glycosphingolipid molecule, a hydroxyl group of the primary alcohol of a sphingosine base is bound to a monosaccharide or an oligosaccharide by a glycoside linkage, to which a fatty acid is further bound by forming an acid-amide linkage. The moiety including the sphingosine base and the fatty acid is referred to as ceramide [Shishitsu no kagaku 365, Tokyo Kagaku Dojin (1974)]. Sphingolipids are widely distributed among animals as an important component of the cell surface layer, and much attention has been paid to its association with blood group substances as well as with various functions such as cell antigenicity, signal transmission, and cell differentiation.

Endoglycoceramidase (EC3.2.1.123), an enzyme which hydrolyses the glycoside linkage between the sugar chain and the ceramide in glycosphingolipid to liberate the sugar chain and the ceramide in their complete forms. Unlike cerebrosidase, this enzyme does not act on cerebroside formed by binding of a monosaccharide to a ceramide. Endoglycoceramidase was first isolated from the Actinomycetes of Rhodococcus strain [The Journal of Biological Chemistry 261, 14278–14282 (1986)]. Rhodococcus strains are also known to produce three different types of endoglycoceramidase (I, II, III) of different substrate specificities [The Journal of Biological Chemistry 264(16) 9510–9519 (1989)].

Other known types of endoglycoceramidase include endoglycoceramidases produced by leech [Biochemical and Biophysical Research Communications 141, 346–352(1986)], earthworm [Biochemical and Biophysical Research Communications 149, 167–172(1987)], bacteria [European Journal of Biochemistry 205, 729–735(1992)], and clam [The FASEB Journal 8, A1439(1994)].

However, it has been extremely difficult to produce endoglycoceramidase in large quantities at high purity by the method using the above producer organisms. This is because the amount of endoglycoceramidase produced by the above producers is very small and because other coexisting enzymes, such as glycosidases and sphingomyelinase, necessitate difficult purification procedures. Thus, there has been a need for a method for producing highly pure enzyme at low cost. There have been reports on the purification of endoglycoceramidase from various organisms. The amino acid sequence and gene structure of endoglycoceramidase, however, have yet to be elucidated, thereby hampering the production of the enzyme by gene engineering technology.

Accordingly, an objective of the present invention is to provide a DNA encoding a polypeptide possessing endoglycoceramidase activity. Another objective of the present invention is to provide a method for producing a highly pure endoglycoceramidase by gene engineering technology using a recombinant having the DNA inserted therein.

SUMMARY OF THE INVENTION

In order to achieve the above objects, the present inventors conducted intensive studies in an effort to isolate the DNA encoding a polypeptide possessing endoglycoceramidase activity for elucidation of its nucleotide sequence. As a result, the present inventors at last succeeded in elucidating the entire nucleotide sequence of DNA encoding a polypeptide possessing endoglycoceramidase activity and in producing highly pure endoglycoceramidase by simple and easy procedures by use of gene engineering technology. Based upon these facts, the present invention has been completed.

In one embodiment, the present invention relates to an isolated DNA having a sequence encoding a polypeptide possessing endoglycoceramidase activity or functionally equivalent variants thereof. Specifically, the isolated DNA comprises a DNA sequence selected from the group consisting of (a) to (d):

(a) a DNA sequence encoding an amino acid sequence of SEQ ID NO:1 or SEQ ID NO:3, or a fragment thereof;

(b) a DNA sequence of SEQ ID NO:2 or SEQ ID NO:4, or a fragment thereof;

(c) a DNA sequence encoding an amino acid sequence resulting from deletion, addition, insertion or substitution of one or more amino acids in the amino acid sequence of SEQ ID NO:1 or SEQ ID NO:3, or a fragment thereof; and (d) a DNA sequence capable of hybridizing to any one of (a) to (c) above.

In another embodiment, the present invention relates to a recombinant DNA which comprises the isolated DNA of the present invention, to a vector which comprises the recombinant DNA, and to a cell of a procaryote or eucaryote transformed with the vector.

In another embodiment, the present invention relates to a method for producing a polypeptide possessing endoglycoceramidase activity or functionally equivalent variants thereof, comprising the steps of:

(a) culturing the cell of the present invention; and (b) recovering the polypeptide possessing endoglycoceramidase activity or functionally equivalent variants thereof from the culture obtained in Step (a).

In another embodiment, the present invention relates to a polypeptide possessing endoglycoceramidase activity or functionally equivalent variants thereof produced by the method of the present invention or encoded by the isolated DNA of the present invention.

In another embodiment, the present invention relates to a synthetic oligonucleotide probe or primer which specifically hybridizes with the isolated DNA of the present invention.

In another embodiment, the present invention relates to an antibody or fragment thereof which specifically binds the polypeptide of the present invention.

The present invention first elucidated the amino acid sequence of endoglycoceramidase II and the nucleotide sequence coding for the enzyme, thereby providing a DNA encoding a polypeptide possessing endoglycoceramidase II activity. The present invention also provides a method for producing the polypeptide possessing endoglycoceramidase II activity on an industrial scale by use of gene engineering technology.

DETAILED DESCRIPTION OF THE INVENTION

Endoglycoceramidase as mentioned herein refers to an enzyme which hydrolyses the glycoside linkage between the sugar chain and ceramide in glycosphingolipid to liberate the sugar chain and the ceramide in their complete forms and includes those derived from various organisms. For example, three different types of endoglycoceramidase are known to be derived from Rhodococcus strain (endoglycoceramidase I, II and III), and these are preferred examples of endoglycoceramidase in the present invention. The activity of endoglycoceramidase can be determined by, for example, the method described in The Journal of Biological Chemistry 267, 1522–1527 (1992), or the method described in The Journal of Biochemistry 264 (16) 9510–9519(1989).

The term "a polypeptide possessing endoglycoceramidase activity" as used in the present specification (sometimes simply referred to as "endoglycoceramidase" as well in the present specification) refers to not only those having an amino acid sequence of native endoglycoceramidase but also its variants due to modification of amino acid sequence by, for example, deletion, substitution, insertion, or addition of amino acid(s), as long as they show the endoglycoceramidase activity when determined by the above- mentioned methods. "Native endoglycoceramidase" used herein includes, but is not limited to, those produced by Rhodococcus strains. Also included are those derived from other microorganisms, such as other Actinomycetes, bacteria, yeasts, fungi, Ascomycetes, and Basidiomycetes, and those derived from plants, animals, insects, and other living things.

The term "functionally equivalent variant" as used herein is defined as follows:

A naturally-occurring protein can undergo amino acid deletion, insertion, addition, substitution and other variations in its amino acid sequence due to modifications, etc. of the protein itself in vivo or during purification, as well as those due to polymorphism and variation of the gene encoding it. It is a well-known fact that there are some such polypeptides which are substantially equivalent to variation-free proteins in terms of physiological and biological activity. A polypeptide which is structurally different from the corresponding protein but has no significant functional difference from the protein is referred to as a functionally equivalent variant.

The same applies to polypeptides prepared by artificially introducing such variations into the amino acid sequence of a protein. Although more diverse variants can be thus obtained, the resulting variants are construed as functionally equivalent variants, as long as their physiological activity is substantially equivalent to that of the original variation-free protein.

For example, the methionine residue at the N-terminus of a protein expressed in *Escherichia coli* is reportedly often removed by the action of methionine aminopeptidase, but some such expressed proteins have the methionine residue and others do not. However, the presence or absence of the methionine residue does not affect protein activity in most cases. It is also known that a polypeptide resulting from replacement of a particular cysteine residue with serine in the amino acid sequence of human interleukin 2 (IL-2) retains IL-2 activity [Science 224, 1431 (1984)].

In addition, in producing a protein by gene engineering, the desired protein is often expressed as a fused protein. For example, the N-terminal peptide chain derived from another protein is added to the N-terminus of the desired protein to enhance the expression of the desired protein, or purification of the desired protein is facilitated by adding an appropriate peptide chain to the N- or C-terminus of the desired protein, expressing the protein, and using a carrier showing affinity for the peptide chain added.

Also, with regards to the codon (triplet base combination) determining a particular amino acid on the gene, 1 to 6 kinds are known to exist for each amino acid. Therefore, there can be a large number of genes encoding an amino acid sequence, though depending on the amino acid sequence. In nature, the gene is not stable, commonly undergoing nucleic acid variation. A variation on the gene may not affect the amino acid sequence to be encoded (silent variation); in this case, it can be said that a different gene encoding the same amino acid sequence has been produced. The possibility is therefore unnegligible that even when a gene encoding a particular amino acid sequence is isolated, a variety of genes encoding the same amino acid sequence are produced with generation passage of the organism containing it.

Moreover, it is not difficult to artificially produce a variety of genes encoding the same amino acid sequence by means of various gene engineering techniques.

For example, when a codon used in the natural gene encoding the desired protein is low in availability in the host used to produce the protein by gene engineering, the amount of protein expressed is sometimes insufficient. In this case, expression of the desired protein is enhanced by artificially converting the codon into another one of high availability in the host without changing the amino acid sequence encoded. It is of course possible to artificially produce a variety of genes encoding a particular amino acid sequence. Such artificially produced different polynucleotides are therefore included in the scope of the present invention, as long as an amino acid sequence disclosed herein is encoded.

Additionally, a polypeptide resulting from at least one change, such as deletion, addition, insertion or substitution, of one or more amino acid residues in the amino acid sequence of the desired protein commonly possesses an activity functionally equivalent to that of the desired protein; genes encoding such polypeptides are also included in the scope of the present invention, whether isolated from natural sources or produced artificially.

In general, genes encoding functionally equivalent variants are often homologous to each other. Nucleic acid molecules capable of hybridizing to a gene of the present invention, and encoding a polypeptide possessing endoglycoceramidase activity, are therefore also included in the scope of the present invention.

The present invention is hereinafter described in detail with reference to endoglycoceramidase II derived from Rhodococcus strain.

First, information regarding a partial amino acid sequence of purified endoglycoceramidase II is obtained. Specifically, endoglycoceramidase II as purified by the method described in The Journal of Biological Chemistry 267, 1522–1527 (1992), for instance, is subjected to the Edman degradation method [The Journal of Biological Chemistry 256, 7990–7997 (1981)] for amino acid sequencing by a conventional method. However, since the N-terminus of endoglycoceramidase II is blocked, it cannot be directly subjected to the amino acid sequencing. After deprotection or releasing the blocked N-terminal amino acid residue, the enzyme is subjected to amino acid sequencing to determine the partial amino acid sequence. Alternatively, the enzyme may be partially hydrolyzed by the action of a highly specific protein hydrolase such as lysylendopeptidase, and the resulting peptide fragments may be separated, purified and subjected to amino acid sequencing. On the basis of the thus-obtained partial amino acid sequence information, the endoglycoceramidase II gene is cloned. For this purpose, a commonly used PCR or hybridization method can be used.

Next, on the basis of the partial amino acid sequence information, synthetic oligonucleotides are designed for use as Southern hybridization probes. Separately, the genomic DNA of Rhodococcus sp. M-777 is completely digested with the appropriate restriction enzymes including MluI, SalI, PstI, and BamHI and subjected to agarose gel electrophoresis for separation [Molecular Cloning, A Laboratory Manual, 2nd ed., T. Maniatis et al., Chapter 6, 3–20, Cold Spring Harbor Laboratory Press, (1989)], and the separated fragments are blotted onto a nylon membrane by a conventional method [Molecular Cloning, A Laboratory Manual, 2nd ed., T. Maniatis et al., Chapter 9, 34, Cold Spring Harbor Laboratory Press, (1989)]. Hybridization can be conducted under commonly used conditions. For example, the nylon membrane is blocked at 65° C. in a prehybridization solution containing 6×SSC (1×SSC is prepared by dissolving 8.77 g NaCl and 4.41 g sodium citrate in 1 L of water), 0.5% SDS, 5× Denhardt's solution (containing bovine serum albumin, polyvinylpyrrolidone and Ficoll, each at 0.1% concentration) and 100 µg/ml salmon sperm DNA, and each $^{32}$P-labeled synthetic oligonucleotide was added, followed by overnight incubation at 65° C. After the nylon membrane is washed in 2×SSC containing 0.1% SDS at 62° C. for 30 minutes, an autoradiogram is taken to detect a DNA fragment that hybridizes to the synthetic oligonucleotide probe. After the DNA fragment corresponding to the band detected is extracted and purified from the gel, the DNA fragment is inserted to a plasmid vector by a commonly used method. Useful plasmid vectors include, but are not limited to, commercially available pUC18, pUC19, pUC119 and pTV118N (all are products of Takara Shuzo).

Then, thus-obtained recombinant plasmid is introduced into a host to transform the host. Usable host cells include procaryotic cells of bacterial (e.g., *Escherichia Coli*), *Bacillus subtilis*, and Actinomyces, and *eucaryotic* cells of yeast, fungi, animals, plants, etc.

When the host is *Escherichia coli*, it may be of a wild strain or a variant strain, as long as it is capable of being transformed and expressing a desired gene. This plasmid introduction can be achieved by a commonly used method, such as the method described in The Molecular Cloning, A Laboratory Manual, 2nd ed., T. Maniatis et al., Cold Spring Harbor Laboratory Press (1989).

Next, a transformant harboring the desired DNA fragment is selected. For this purpose, the characteristics of the plasmid vector are utilized. In the case of pUC19, for instance, colonies having a foreign gene introduced thereto are selected by selecting ampicillin-resistant colonies on an ampicillin-containing plate, or selecting ampicillin-resistant white colonies on a plate containing ampicillin, 5-bromo-4-chloro-3-indolyl-β-D-galactoside (X-Gal) and isopropyl-β-D-thiogalactopyranoside (IPTG).

Next, the colony having a vector containing the desired DNA fragment is then selected out of the above population. This selection is achieved by using colony hybridization [Molecular Cloning, A Laboratory Manual, 2nd ed., T. Maniatis et al., Chapter 1, 90–104 of the Cold Spring Harbor Laboratory Press, (1989)] or plaque hybridization [Molecular Cloning, A Laboratory Manual, 2nd ed., T. Maniatis et al., Chapter 2, 108–117, Cold Spring Harbor Laboratory Press (1989)], chosen appropriately according to vector types. PCR methods [Molecular Cloning, A Laboratory Manual, 2nd ed., T. Maniatis et al., Chapter 14, 15–19, Cold Spring Harbor Laboratory Press, (1989)] are also applicable.

Once the vector containing the desired DNA fragment is selected, the nucleotide sequence of the desired DNA fragment inserted in this vector is determined by an ordinary method, such as the dideoxy chain terminator method [Molecular Cloning, A Laboratory Manual, 2nd ed., T. Maniatis et al., Chapter 13, 3–10, Cold Spring Harbor Laboratory Press (1989)]. The thus-determined nucleotide sequence is compared with partial amino acid sequence, molecular weight, etc. of endoglycoceramidase II to know the gene structure and entire amino acid sequence of endoglycoceramidase II.

When the obtained DNA fragment does not contain the full-length endoglycoceramidase II, the full-length endoglycoceramidase II can be obtained by digesting genomic DNA of Rhodococcus sp. M-777 with other restriction enzymes, obtaining the lacking portion from the digests by hybridization, etc. using a part of the DNA fragment obtained above as a probe, then joining the lacking portion.

The entire or part of the resulting endoglycoceramidase II gene as obtained above is inserted to an appropriate plasmid vector, which is then transformed into a host cell. The transformant thus obtained is cultured under commonly used conditions to produce a polypeptide possessing endoglycoceramidase II activity.

For example, when *Escherichia coli* and pTV118N are used as a host cell and plasmid vector, respectively, the transformant is cultured at 37° C. overnight in an L medium [0.1% Trypton, 0.05% yeast extract, 0.1% NaCl, pH 7.2) containing 100 µg/ml ampicillin; upon reach of an absorbance at 600 nm of about 0.5, IPTG is added, followed by further 4-hour culture at 37° C. Then, the cells are recovered, lysed, and disrupted by ultrasonication, etc. to solubilize the desired endoglycoceramidase II produced and accumulated in the cells, and then centrifuged to obtain the supernatant as a cell-free extract solution of endoglycoceramidase II. There may be the case where the desired enzyme expressed can be produced in the form of inclusion body.

The expression of the gene product can be confirmed by, for example, determining endoglycoceramidase II activity. When the recombinant is *Escherichia coli*, for example, activity can be determined by the method described in the Journal of Biological Chemistry 267, 1522–1527 (1992), using the extract of the recombinant *Escherichia coli* as an enzyme solution, or by the method described in The Journal of Biological Chemistry 264 (16) 9510–9519 (1989) where the activity is measured by the method of Park and Johnson using purified asialo-GM1 as the substrate.

When the desired expression of endoglycoceramidase II is noted, optimum conditions for endoglycoceramidase II expression are examined.

Endoglycoceramidase II can be purified from the transformant culture by an ordinary method. That is, the transformant cells are collected by centrifugation, disrupted by ultrasonication, or the like, and then subjected to centrifugation, etc. to yield a cell-free extract, which can be purified by common protein purification methods, such as salting-out and various chromatographies including ion exchange, gel filtration, hydrophobic interaction and affinity chromatographies. Depending on the host-vector system used, the expression product is extracellularly secreted by the transformant; in this case, the product can be purified from the culture supernatant in the same manner as that described above. When the host is *Escherichia coli*, the expression product is sometimes formed as an insoluble inclusion body. In this case, cells are collected by centrifugation after cultivation, disrupted by ultrasonication, or the like, then subjected to centrifugation, etc. to separate the insoluble fraction containing the inclusion body. After being washed, the inclusion bodies are solubilized with a commonly used protein solubilizer, such as detergent urea, or guanidine hydrochloride, followed by purification by various chromatographies, such as ion exchange, gel filtration, hydrophobic interaction and affinity chromatographies, as necessary, after which a refolding treatment by dialysis or dilution is conducted to yield a preparation of endoglycoceramidase II retaining its activity. This preparation may be purified by various chromatographies to yield a highly pure preparation of endoglycoceramidase II.

The DNA of the present invention is an isolated DNA having a DNA segment encoding a polypeptide possessing such endoglycoceramidase activity, and is exemplified by the DNA having a DNA segment encoding the amino acid sequence of SEQ ID NO:1 set forth in the sequence listing. It is also exemplified by a DNA having a DNA segment encoding a portion of the amino acid sequence of SEQ ID No:1 set forth in the sequence listing which possesses endoglycoceramidase activity or functionally equivalent activity. Examples of such DNAs include that of SEQ ID NO:2 set forth in the sequence listing, and a portion thereof containing a nucleotide sequence encoding a polypeptide possessing endoglycoceramidase activity.

In the present invention, DNA which hybridizes to the above DNAs and which encodes a polypeptide possessing endoglycoceramidase activity or functionally equivalent variant thereof is also included. Also, the genes of the present invention include genes with or without a sequence encoding a signal sequence. For example, the entire amino acid sequence (including a signal sequence) of endoglycoceramidase II is set forth in SEQ ID NO:1; its DNA sequence, in SEQ ID NO:2. The entire amino acid sequence (sequence from the N-terminus, not including a signal sequence) of endoglycoceramidase II is set forth in SEQ ID NO:3; its DNA sequence, in SEQ ID NO:4.

The DNA of the present invention, which encodes a polypeptide possessing endoglycoceramidase activity, can also be obtained from a gene or cDNA derived from other cells by hybridization using the nucleotide sequence of the present invention. In this case, the following method, for instance, is applicable.

First, chromosomal DNA obtained from the desired gene source, or cDNA prepared from mRNA by means of reverse transcriptase, is joined to a plasmid or phage vector and introduced into a host to yield a library by a conventional method. The library is then cultured on a plate; the resulting colonies or plaques are transferred onto a nitrocellulose or nylon membrane and subjected to denaturing treatment to immobilize the DNA to the membrane. This membrane is incubated in a solution containing a probe labeled with $^{32}P$ or the like (the probe used may be any gene encoding the amino acid sequence set forth in SEQ ID NO:1 or SEQ ID NO:3 in the sequence listing, or a portion thereof; for example, the genes set forth in SEQ ID NO:2 or SEQ ID NO:4, or a portion thereof can be used) to form a hybrid between the DNA on the membrane and the probe.

For example, the membrane with DNA immobilized thereon is subjected to hybridization with the probe in a solution containing 6×SSC, 1% SDS, 100 µg/ml salmon sperm DNA and 5×Denhardt's solution at 65° C. for 20 hours. After hybridization, the nonspecifically adsorbed portion is washed out, followed by autoradiography, etc. to identify clones that formed a hybrid with the probe. This procedure is repeated until only a single clone has formed the hybrid. The clone thus obtained has a gene encoding the desired protein inserted therein.

The nucleotide sequence of the gene obtained is then determined by, for example, the following method, to confirm if the gene obtained is identical with the desired gene encoding a polypeptide possessing endoglycoceramidase activity. When the recombinant is *Escherichia coli*, base sequencing for a clone obtained by hybridization can be achieved by culturing the *Escherichia coli* in a test tube, or the like, extracting the plasmid by a conventional method, digesting the extracted plasmid with restriction enzymes, separating the insert and subcloning it into M13 phage vector, or the like, and determining the base sequence by the dideoxy method. When the recombinant is a phage, basically the same procedure as that used above can be used to determine the nucleotide sequence. Basic experimental techniques for from cultivation to base sequencing are described in, for example, Molecular Cloning, A Laboratory Manual, 2nd. ed., T. Maniatis et al., Cold Spring Harbor Laboratory Press (1989).

The identity of the gene thus obtained as the desired gene encoding a polypeptide possessing endoglycoceramidase activity can be confirmed by comparing the base sequence with that of the endoglycoceramidase gene of the present invention and the amino acid sequence set forth in SEQ ID NO:1 or SEQ ID NO:3 in the sequence listing.

If the gene obtained does not contain the entire region encoding a polypeptide possessing endoglycoceramidase activity, the nucleotide sequence of the entire region encoding a polypeptide possessing endoglycoceramidase activity that hybridizes to the endoglycoceramidase gene of the present invention can be determined by preparing a synthetic DNA primer from the gene obtained, and amplifying the lacking region by PCR or by screening the DNA library or cDNA library using the gene fragment obtained as a probe.

A polypeptide possessing endoglycoceramidase activity can be obtained by gene engineering technology as follows:

First, a DNA encoding a polypeptide possessing endoglycoceramidase activity as obtained above is joined to an expression vector which is capable of expressing the gene in an appropriate host cell, such as *Escherichia coli*, *Bacillus subtilis*, actinomyces, yeast, fungi, animal cell, insect cell or plant cell, by a conventional method, followed by introduction to the host cell, to yield a recombinant. By culturing this recombinant, a polypeptide possessing endoglycoceramidase activity can be produced. There is a possibility that endoglycoceramidase derived from eukaryotic organisms has a sugar chain. By the use of a cell incapable of sugar chain biosynthesis as a host, e.g., prokaryotic organisms, such as *Escherichia coli* and *Bacillus subtilis*, Actinomyces or by the use of a variant yeast, fungi, animal, insect or plant cell which has lost its capability of sugar chain biosynthesis, a polypeptide possessing endoglycoceramidase activity and no sugar chains can be expressed.

In some expression systems, the expressed endoglycoceramidase is accumulated in the recombinant cell in the form of insoluble inclusion body. In this case, after the inclusion body is recovered and solubilized under mild conditions, e.g., with urea, the denaturant is removed to restore the original activity of the enzyme. Expression can be confirmed by determining endoglycoceramidase activity by the method as described above.

A polypeptide possessing endoglycoceramidase activity can be purified from a recombinant by ordinary chromatographic techniques. For example, when the desired polypeptide is solubilized after disruption of the cells, the supernatant is subjected to chromatography, such as hydrophobic interaction, ion exchange or gel filtration chromatography, to obtain the desired polypeptide as expressed. When the desired polypeptide is accumulated in the recombinant in an insoluble form, cultured cells are disrupted, after which the precipitate is recovered and solubilized with a denaturant, such as urea. The denaturant is then removed, followed by refolding and subsequent chromatographic treatment as described above to obtain a polypeptide of desired activity.

The present invention provides the primary structure of endoglycoceramidase II, and the gene structure thereof. The elucidation of the gene structure of the present invention permits the production of a polypeptide possessing endoglycoceramidase activity by gene engineering. By the present method using gene engineering technology, a highly pure polypeptide preparation possessing endoglycoceramidase activity can be produced at low cost.

EXAMPLES

The following examples illustrate the present invention but are not intended to limit the invention in any manner.

Example 1

Cloning of Endoglycoceramidase II Structural Gene (1) Extraction and purification of genomic DNA Rhodococcus sp. M-777, an endoglycoceramidase II producer, was inoculated to 900 ml of a medium (pH 7.0) comprising 1.5% mycological peptone (produced by OXOID), 0.2% NaCl and 0.1% yeast extract, and subjected to shaking culture at 28° C. for 3 days. After completion of the cultivation, the culture broth was centrifuged; cells were collected and suspended in 4.5 ml of a buffer (pH 8.0) containing 10 mM Tris-HCl and 20 mM EDTA, then frozen and thawed. To this cell suspension, 2.5 ml of a buffer (pH 8.0) containing 50 mM Tris-HCl, 50 mM EDTA and 4 mg/ml lysozyme was added, followed by incubation at 30° C. for 16 hours. To this mixture, 10 ml of an extracting buffer (50 mM Tris-HCl, 1% SDS, 0.4 mg/ml proteinase K, pH 7.5) was added, followed by incubation at 50° C. for 16 hours, after which 10 ml of another extracting buffer was added, followed by incubation for 16 hours. After the incubation mixture was allowed to cool to room temperature, an equal volume of a phenol/chloroform solution, previously saturated with TE buffer (10 mM Tris-HCl, 1 mM EDTA, pH 8.0), was added, followed by gentle rotary shaking for 16 hours and subsequent centrifugation at 3,500 rpm for 30 minutes, after which the supernatant was recovered. This solution was dialyzed against a 10 mM Tris-HCl buffer (pH 8.0) containing 5 mM EDTA at 4° C. to yield a genomic DNA solution.

(2) Partial amino acid sequencing of endoglycoceramidase II

Endoglycoceramidase II was first purified by the method described in the Journal of Biological Chemistry, 267, 1522–1527 (1992). The N-terminal amino acid sequence of purified endoglycoceramidase II could not be determined by the Edman degradation method due to N-terminal blockade.

With this finding in mind, the internal amino acid sequence was determined as follows:

To a test tube containing 4 μl of pyridine, 1 μl of 4-vinylpyridine, 1 μl of tributylphosphine and 5 μl of distilled water, a smaller sample tube containing the purified endoglycoceramidase II was inserted, and the outer tube was vacuum sealed, followed by heating at 100° C. for 5 minutes to pyridylethylate the cysteine residues in the endoglycoceramidase II in a gas phase. A 1 nmol sample of endoglycoceramidase II thus S-pyridylethylated was dissolved in 50 μl of a 20 mM Tris buffer (pH 9.0) containing 4M urea; 8 pmol of lysylendopeptidase (produced by Pierce) was added, followed by digestion at 37° C. for 16 hours. Reverse-phase chromatography was then conducted on a density gradient from distilled water containing 0.065% trifluoroacetic acid (TFA) to acetonitrile containing 0.05% TFA through a μRPC C2/C18 SC2.1/10 column (produced by Pharmacia) using a SMART system (produced by Pharmacia), to purify the peptide fragment.

The purified peptide fragment was analyzed by the Edman degradation method using a model 477 gas-phase peptide sequencer (produced by Applied Biosystems) to determine the partial amino acid sequences EGC1 (SEQ ID NO:5), EGC2 (SEQ ID NO:6), EGC4 (SEQ ID NO:7), EGC5 (SEQ ID NO:8), EGC7 (SEQ ID NO:9), EGC8 (SEQ ID NO:10) and EGC11 (SEQ ID NO:11).

(3) Cloning of DNA fragment containing endoglycoceramidase II gene

The genomic DNA prepared in Example 1 (1) above, 30 μg, was digested with restriction enzymes MluI, PstI and SalI, each 100 U, at 37° C. for 6 hours; after additional 100 U of each enzyme was added, the reaction was continued for 16 hours. This reaction mixture, in an amount equivalent to 5 μg of DNA, was subjected to 0.7% agarose gel electrophoresis, after which the DNA was transferred onto a nylon membrane (Hybond-N$^+$, produced by Amersham) by the Southern blotting method [Idenshi Kenkyuhou II, 218–221, published by Tokyo Kagaku Dojin). This membrane was provided in duplicate.

The hybridization probes used were the synthetic oligonucleotides EGIH1 (SEQ ID NO:12) and EGIH2 (SEQ ID NO:13) synthesized on the basis of the partial amino acid sequence EGC1 determined in Example 1 (2). These synthetic oligonucleotides, each 5 pmol, were labeled with $^{32}$P using the MEGARABEL™ (produced by Takara Shuzo) to yield labeled probes. Each of the pair of membranes prepared above was subjected to prehybridization at 65° C. for 5 hours in a solution containing 6×SSC (1×SSC is an aqueous solution of 8.77 g of NaCl and 4.41 g of sodium citrate in 1 L of water), 0.5% SDS, 100 μg/ml herring sperm DNA and 5×Denhardt's (containing bovine serum albumin, polyvinylpyrrolidone and Ficoll, each at 0.1% concentration), after which each labeled probe was added to a concentration of 0.5 pmol/ml, followed by overnight hybridization at 65° C. Each membrane was then washed in 6×SSC at room temperature for 10 minutes, in 2×SSC and 0.1% SDS at room temperature for 10 minutes, and in 0.2×SSC and 0.1% SDS at 62° C. for 30 minutes; after excess solution was removed, each filter was exposed to an imaging plate (produced by Fuji Photo Film) for 3 hours, and the image was detected using a BAS2000 imaging analyzer (produced by Fuji Photo Film).

As a result, bands hybridizing to the synthetic oligonucleotide EGIH1 (used as a probe) appeared at positions corresponding to about 4.4 kbp for the MluI digest, about 1.9 kbp for the PstI digest, and about 1.2 kbp for the SalI digest. Also, a large number of non-specific bands hybridizing to the synthetic oligonucleotide EGIH2 were detected, in addition to the band detected with the synthetic oligonucleotide EGIH1. With this finding in mind, the MluI digest was used for the experiments that followed.

To a digest of pUC19 (produced by Takara Shuzo) with restriction enzyme HincII, a phosphorylated MluI linker (produced by Takara Shuzo) was inserted and ligated, to construct a plasmid having a newly introduced MluI site, which was designated as pUC19M. The genomic DNA digested with restriction enzyme MluI, 20 μg, was subjected to 0.7% agarose gel electrophoresis; an agar portion corresponding to the band appearing in the above-described hybridization was cut out and subjected to extraction and purification using the EASYTRAP™ (produced by Takara Shuzo); the resulting DNA fragment was inserted and ligated to a pUC19M digest with restriction enzyme MluI.

*Escherichia coli* JM109 was transformed with this plasmid, after which it was cultured on 5 round petri dishes 8.5 cm in diameter containing an L-agar medium containing 100 μg/ml ampicillin until 200 to 1,000 colonies per dish were formed. From these dishes, 500 colonies were selected and transferred onto a nylon membrane (Hybond-N⁺, produced by Amersham) on a plate of the same medium. After incubation at 37° C. for 3 hours, this nylon membrane was kept on filter paper immersed in a solution comprising 0.5M NaOH and 1.5M NaCl for 5 minutes (denaturation) and on filter paper immersed in a solution comprising a 0.5M Tris-HCl buffer (pH 7.0) and 3M NaCl for 5 minutes (neutralization), followed by rinsing with 2×SSC. Using this nylon membrane and the synthetic oligonucleotide EGIH1 (SEQ ID NO:12) as a probe, hybridization was conducted under the same conditions as those described above; two clones with positive signal were obtained. These *Escherichia coli* JM109 clones were designated as 1–25 and 3–6, respectively. From these clones, plasmid DNAs were separated and purified by the alkali lysis method (Molecular Cloning, A Laboratory Manual, 2nd ed., T. Maniatis et al., Chapter 1, 25–28, Cold Spring Harbor Laboratory, 1989), and designated as pEGCM125 and pEGCM36, respectively. These were digested with several restriction enzymes (MluI, EcoRI, HindIII) and electrophoresed to analyze for cleavage pattern. As a result, pEGCM125 was found to have two MluI inserts.

With this finding in mind, pEGCM36 was used for the experiments that followed.

pEGCM36 was digested with 24 restriction enzymes and electrophoresed to analyze for cleavage pattern. Also, colonies were transferred onto a nylon membrane (Hybond-N⁺, produced by Amersham) by the Southern blotting method as described above, followed by hybridization using the synthetic nucleotide EGIH1 (SEQ ID NO:12) as a probe under the same conditions as those described above. Of the bands which hybridized to the probe, the about 1 kbp DNA fragment obtained by digestion with restriction enzyme HincII and the about 1.1 kbp DNA fragment obtained by digestion with restriction enzyme KpnI were purified by agarose gel electrophoresis and subcloned into the HincII site or KpnI site of pUC19, respectively. The resulting plasmids were designated as pM36H and pM36K, respectively. These plasmids were further digested with appropriate restriction enzymes (PstI, SphI, SmaI/NaeI) and subjected to self-ligation using a DNA ligation kit (produced by Takara Shuzo) to yield various deletion variants.

The nucleotide sequences of these deletion variants and pM36H, pM36K and pEGCM36 were determined from their end by the dideoxy chain terminator method (Molecular Cloning, A Laboratory Manual, 2nd edition, edited by T. Maniatis et al., Chapter 13, 3–10, Cold Spring Harbor Laboratory, 1989); it was shown that the pM36H insert and the pM36K insert overlapped with each other at an end of the pEGCM36 insert. It was also shown that the nucleotide sequences encoding the partial amino acid sequences EGC1 (SEQ ID NO:5), EGC2 (SEQ ID NO:6), EGC4 (SEQ ID NO:7), EGC5 (SEQ ID NO:8), EGC8 (SEQ ID NO:10) and EGC11 (SEQ ID NO:11) are present on the same frame, and that a DNA sequence encoding a signal peptide-like sequence is present upstream the frame.

However, none of the nucleotide sequences determined here had any sequence encoding the partial amino acid sequence EGC7 (SEQ ID NO:9), nor were there any stop codons downstream the frame encoding the partial amino acid sequences EGC1, EGC2, EGC4, EGC5, EGC8 and EGC11.

(4) Cloning of DNA fragment containing the gene encoding C-terminal region of endoglycoceramidase II To cover the entire length of the endoglycoceramidase II gene, a DNA fragment encoding the portion near the C-terminus, which was lacked in pEGCM36, was screened for by the Southern hybridization method in the same manner as in Example 1 (3) above. The probe used was the about 200 bp fragment obtained by HincII digestion of pM36K, which contains the DNA sequence nearest to the C-terminus. Specifically, pM36K was digested with HincII and subjected to 1% agarose gel electrophoresis; the resulting about 200 bp DNA fragment was cut out.

This HincII digest fragment was subjected to extraction and purification using the SpinBind™ (produced by Takara Shuzo); the resulting purified DNA fragment was labeled with ³²P using a BcaBEST™ labeling kit (produced by Takara Shuzo) to yield a labeled probe. The genomic DNA prepared in Example 1 (1) above, 50 μg, was digested with restriction enzymes BamHI, PstI and HincII, each 180 U, at 37° C. for 6 hours. From this reaction mixture, in an amount equivalent to 10 μg of DNA, membranes were prepared in the same manner as in Example 1 (3) above. Each membrane was subjected to prehybridization at 68° C. for 3 hours in a solution containing 6×SSC (1×SSC is an aqueous solution of 8.77 g of NaCl and 4.41 g of sodium citrate in 1 L of water), 0.5% SDS, 100 μg/ml herring sperm DNA and 5×Denhardt's (containing bovine serum albumin, polyvinylpyrrolidone and Ficoll, each at 0.1% concentration), after which the labeled probe was added to a concentration of 0.1 pmol/ml, followed by overnight hybridization at 68° C. Each filter was then washed in 6×SSC at room temperature for 10 minutes, in 2×SSC and 0.1% SDS at room temperature for 10 minutes, and in 0.2×SSC and 0.1% SDS at 70° C. for 30 minutes. A solution was removed, each filter was exposed to an imaging plate (produced by Fuji Photo Film) for 10 minutes and the image was detected using a BAS2000 imaging analyzer (produced by Fuji Photo Film).

As a result, bands hybridizing to the probe appeared at positions corresponding to about 2.7 kbp for the BamHI digest, about 1.3 kbp for the PstI digest, about 0.3 kbp for the HincII digest. The genomic DNA digested with BamHI, 20 μg, was subjected to 0.7% agarose gel electrophoresis; an agar portion corresponding to the band noted at about 2.7 kbp in the above hybridization was cut out, subjected to extraction and purification using the EASYTRAP™ (produced by Takara Shuzo); the resulting DNA fragment was inserted to the BamHI site of pUC19.

After *Escherichia coli* JM109 was transformed with this plasmid, it was cultured overnight on 10 round petri dishes 8.5 cm in diameter containing an L agar medium containing 100 μg/ml ampicillin until 200 to 500 colonies per dish were formed. From these dishes, 500 colonies were selected and transferred onto a nylon membrane (Hybond-N⁺, produced by Amersham) on a plate of the same medium. After incubation at 37° C. for 10 hours, this nylon membrane was kept on filter paper immersed in a solution comprising 0.5M NaOH and 1.5M NaCl for 5 minutes (denaturation) and on filter paper immersed in a solution comprising a 0.5M Tris-HCl buffer (pH 7.0) and 3M NaCl for 5 minutes (neutralization), followed by rinsing with 2×SSC. Using this nylon membrane and the about 200 bp HincII fragment of pM36K as a probe, in the same manner as above, hybridization was conducted under the same conditions as those described above; one clone showing a positive signal was obtained. The plasmid DNA of this clone was prepared by the alkali lysis method and designated as pEGCB20.

This clone was digested with several restriction enzymes (BamHI, EcoRI, HincII, HindIII, KpnI, PstI, SacI, SalI, SmaI, SphI, XbaI) and electrophoresed to analyze for cleavage pattern. Also, colonies were transferred onto a nylon membrane (Hybond-N+, produced by Amersham) by the Southern blotting method as described above, followed by hybridization using the about 200 bp HincII fragment of pM36K as a probe under the same conditions as those described above. Of the bands which hybridized to the probe, the about 1 kbp DNA fragment obtained by digestion with restriction enzyme SphI was purified by agarose gel electrophoresis and subcloned into the SphI site of pUC19; the resulting plasmid was designated as pBS1K. This plasmid was further digested with appropriate restriction enzymes (MluI, NaeI, SphI) and subcloned.

The nucleotide sequences of these subclones and pBS1K were determined from their end by the dideoxy method. As a result, the base sequence of the about 200 bp HincII fragment of pM36K appeared, with the nucleotide sequence encoding the partial amino acid sequence EGC7 (SEQ ID NO:9). In addition, a 1473 bp open reading frame (ORF) was found over the region between the MluI insert of pEGCM36 and the BamHI insert of pEGCB20, both determined in Example 1 (3) above. Within this ORF, all the nucleotide sequences encoding amino acid sequences of endoglycoceramidase II determined in Example 1 (2) above were found.

On the basis of the above results, the entire nucleotide sequence and primary structure of the endoglycoceramidase II gene were determined. The results are given in FIG. 1, in which the restriction enzyme maps for the pM36H, pM36K and pBS1K inserts and the positions of these inserts and the endoglycoceramidase II gene are shown. An example nucleotide sequence of the ORF of the endoglycoceramidase II gene is set forth in SEQ ID NO:2 in the sequence listing. The amino acid sequence of the polypeptide encoded by the endoglycoceramidase II gene is set forth in SEQ ID NO:1 in the sequence listing.

As known from SEQ ID NO:1 and SEQ ID NO:2 in the sequence listing, in the endoglycoceramidase gene, the base sequence which corresponds to the initiation codon is GTG.

Example 2
Construction of Plasmid for Expression of Endoglycoceramidase II

A plasmid for endoglycoceramidase II expression in *Escherichia coli* was constructed by isolating the endoglycoceramidase II structural gene from pEGCM36 and pEGCB20 as obtained in Example 1, in which said structural gene is present in two portions, ligating it to a plasmid appropriate for its expression in *Escherichia coli*, and introducing the ligation product to an *Escherichia Coli* cell. The same principle applies to other host cells; a plasmid for endoglycoceramidase II expression in any selected host cell can be constructed by isolating the endoglycoceramidase II structural gene from pEGCM36 and pEGCB20, in which the structural gene is present in two portions, ligating it to a plasmid appropriate for its expression in the host cell, and introducing the ligation product into the host cell.

Figure 1A:
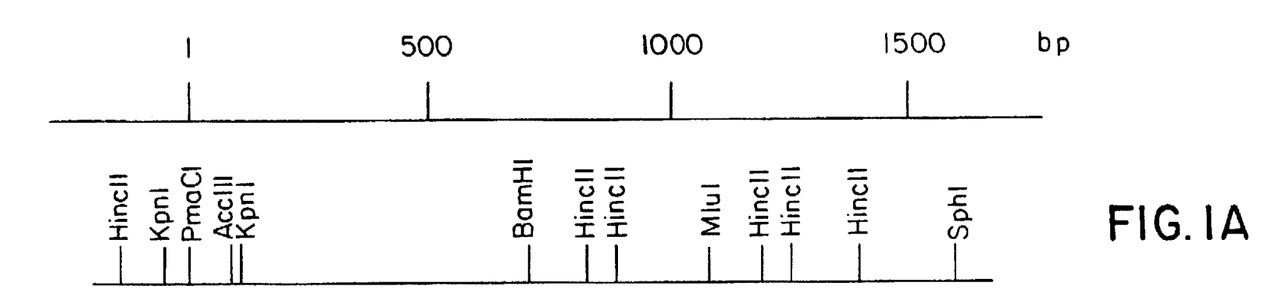
FIG. 1 shows restriction enzyme maps of the fragments inserted to pM36H, pM36K and pBS1K, and the locations of each inserts and the gene encoding endoglycoceramidase (EGCase) II.
Figure 1B:
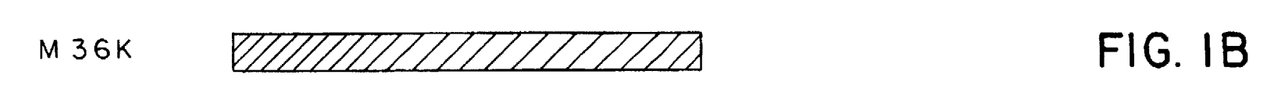
Figure 1C:
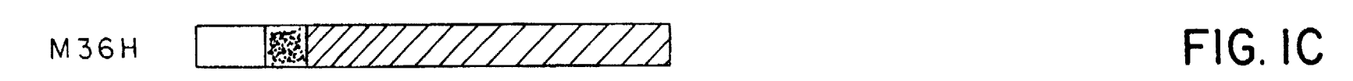
Figure 1D:
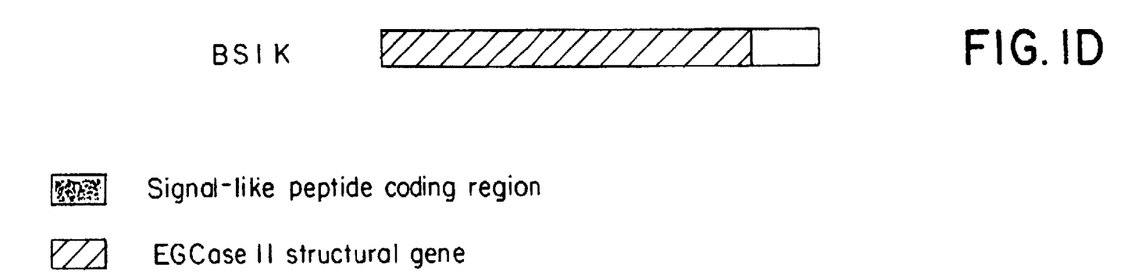
Figure 2:
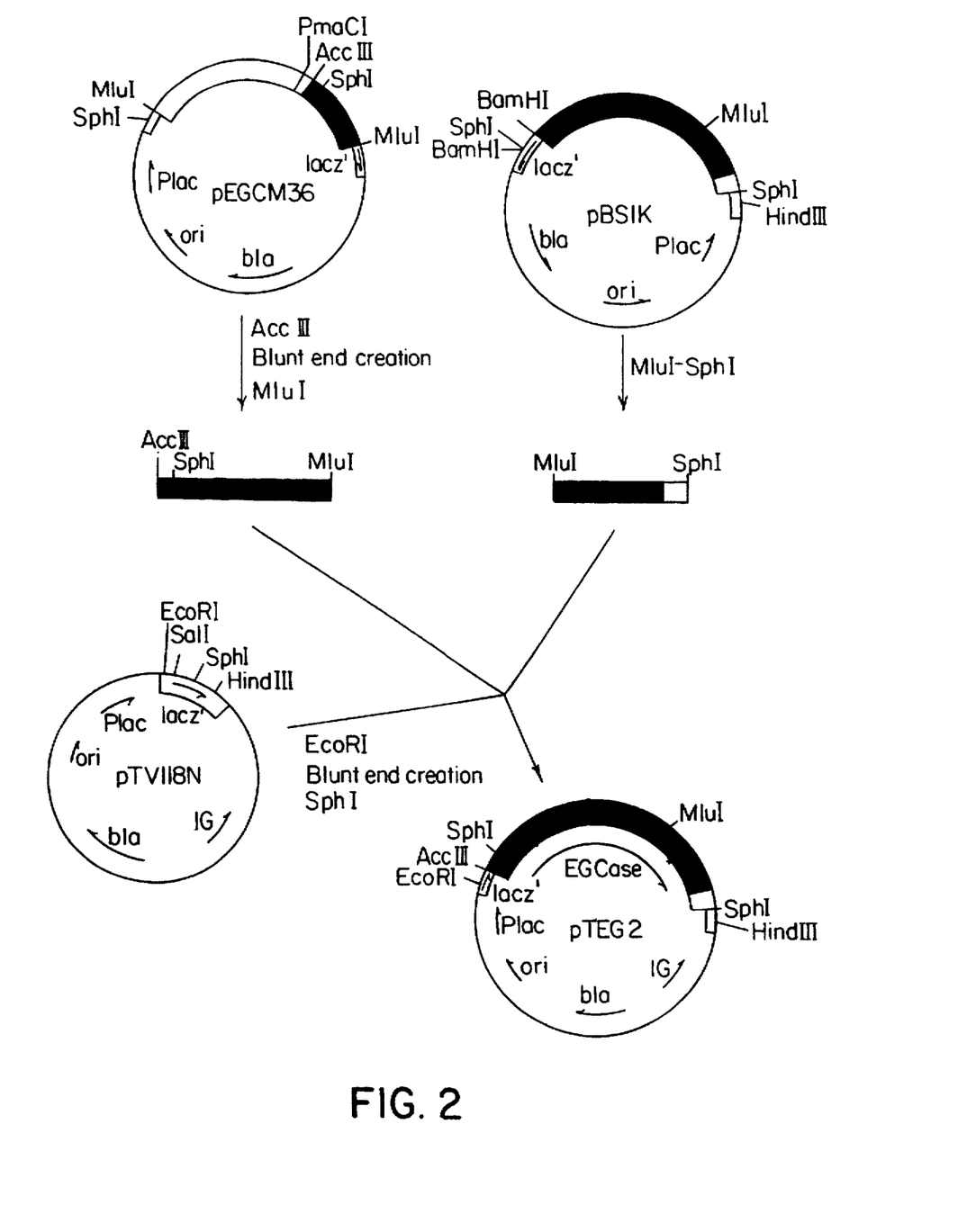
FIG. 2 is a construction diagram of plasmid pTEG2.

First, pEGCM36 was digested with restriction enzyme AccIII, followed by terminal blunting using a DNA blunting kit (produced by Takara Shuzo) and subsequent further digestion with restriction enzyme MluI, after which it was subjected to agarose gel electrophoresis, followed by extraction and purification from the gel, to yield an about 1 kbp EGCM36-AccIII/MluI fragment. Separately, pBS1K obtained from pEGCB20 by subcloning in Example 1 was digested with restriction enzymes MluI and SphI and subjected to agarose electrophoresis, after which an about 500 bp BS1K-MluI/SphI was cut out and extracted. These EGCM36-AccIII/MluI and BS1K-MluI/SphI fragments were simultaneously ligated and inserted to pTV118N (produced by Takara Shuzo) to yield pTEG2, the pTV118N being previously digested with restriction enzyme EcoRI, terminus-blunted, and further digested with restriction enzyme SphI (FIG. 2).

Since this plasmid contains a sequence encoding 6 amino acid residues (SEQ ID NO:14) including a lacZα-derived peptide, upstream the N-terminus side of the region en coding endoglycoceramidase II without the signal-like sequence, it is expected that expression of endoglycoceramidase II as a fusion complex with lacZα can be induced using the SD sequence and initiation codon of lacZ.

Figure 3:
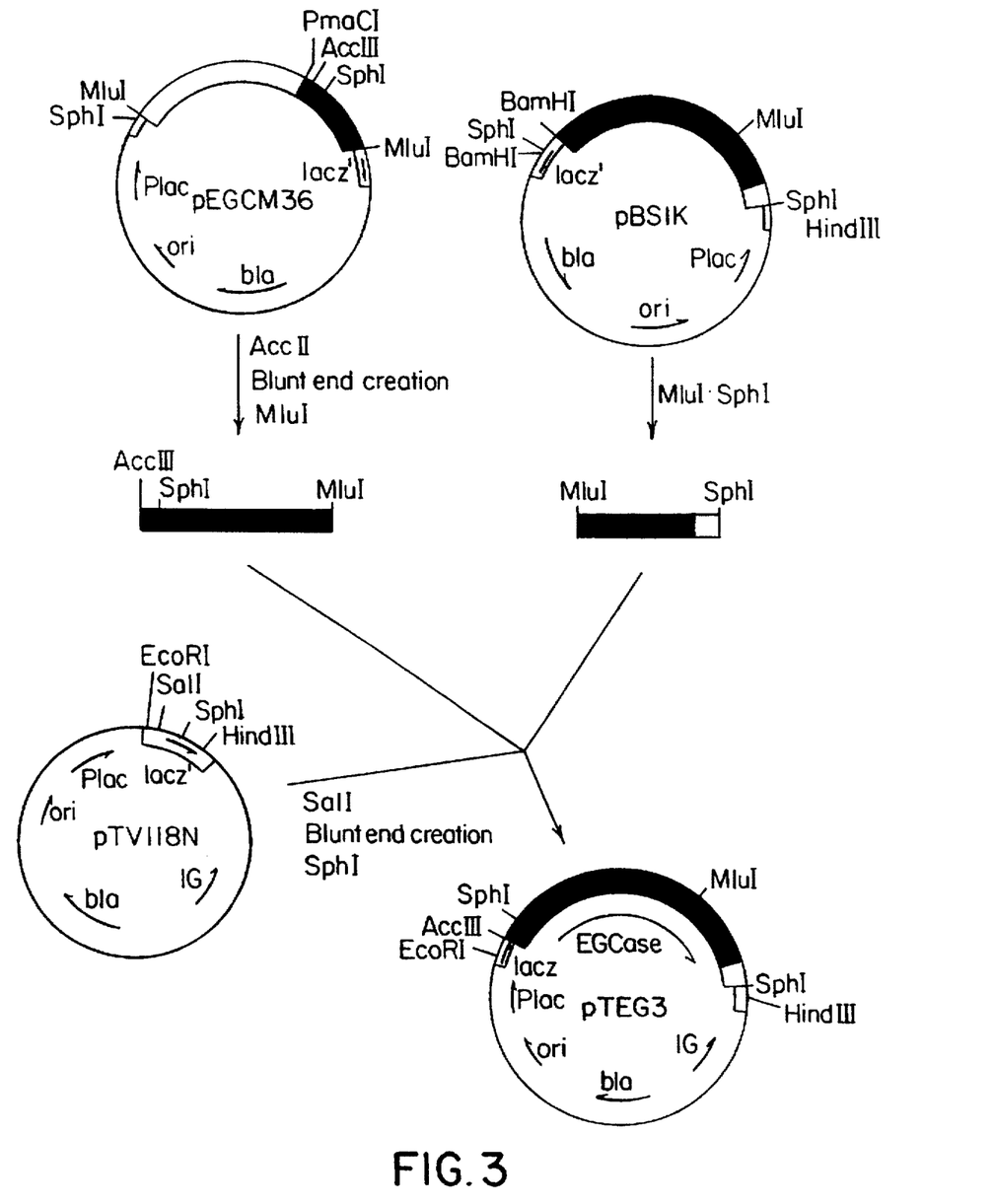
FIG. 3 is a construction diagram of plasmid pTEG3.

Similarly, the EGCM36-AccIII/MluI and BS1K-MluI/SphI fragments were simultaneously ligated and inserted to PTV118N (produced by Takara Shuzo) to yield pTEG3, the pTV118N being previously digested with restriction enzyme SalI, terminus-blunted, and further digested with restriction enzyme SphI(FIG. 3). This plasmid contains a sequence encoding 18 amino acid residues (SEQ ID NO:15), including a lacZα-derived peptide, upstream the N-terminus side of the region encoding endoglycoceramidase II without the signal-like sequence.

An expression plasmid including the signal-like sequence was constructed.

pM36H as obtained in Example 1 was digested with restriction enzymes AccIII and PmaCI and subjected to agarose gel electrophoresis, followed by extraction and purification from the gel, to yield an about 90 bp M36H-AccIII-PmaCI fragment.

Figure 4:
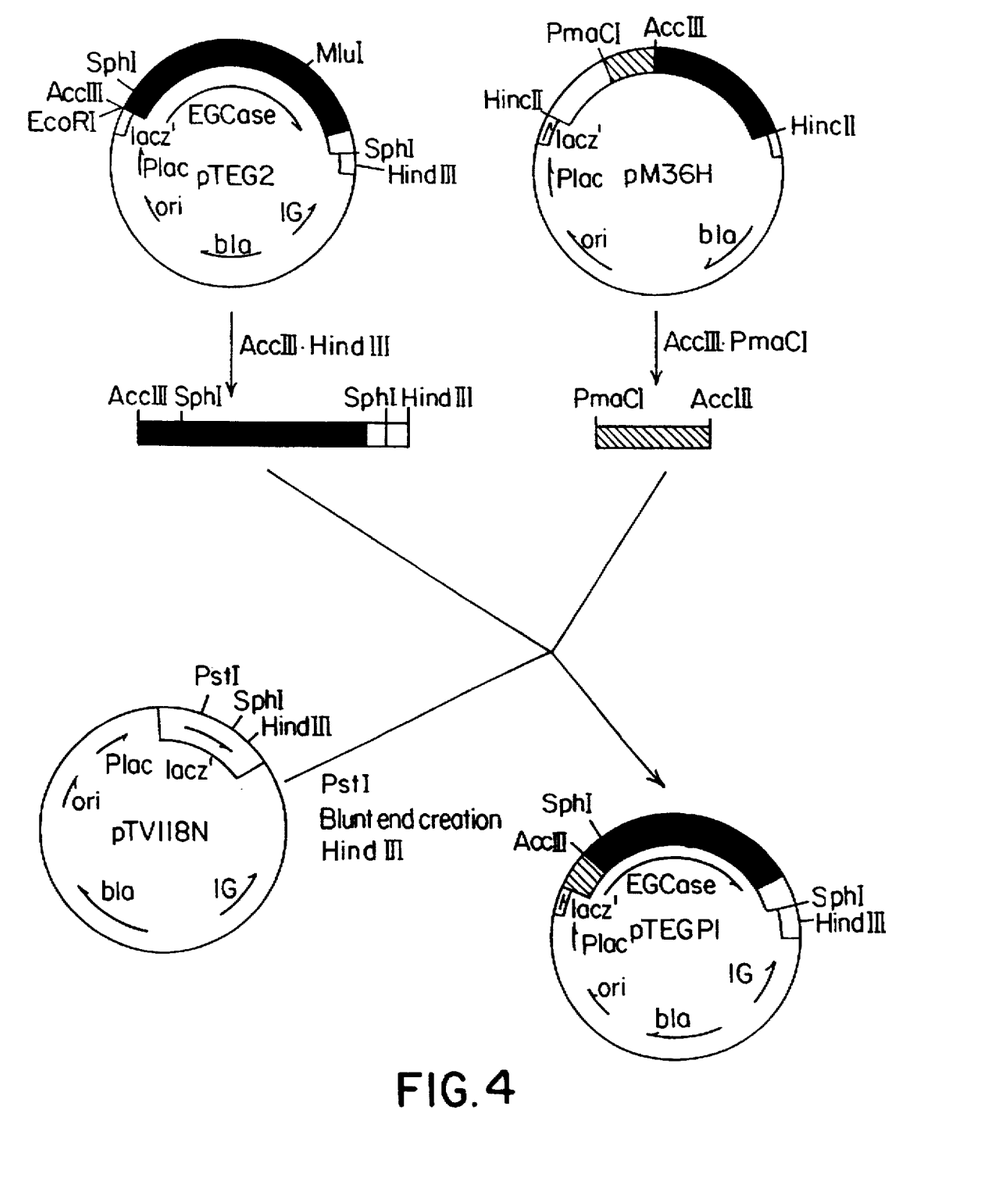
FIG. 4 is a construction diagram of plasmid pTEGP1.

Also, pTEG2 described above was digested with restriction enzymes AccIII and HindIII and subjected to agarose gel electrophoresis, followed by extraction and purification from the gel, to yield an about 1.6 kbp TEG2-AccIII/HindIII fragment. These M36H-AccIII/PmaCI and TEG2-AccIII/HindIII fragments were simultaneously ligated and inserted to pTV118N to yield pTEGP1, the pTV118N being previously digested with restriction enzyme PstI, terminus-blunted and further digested with restriction enzyme HindIII (FIG. 4).

*Escherichia coli*, as a host, was transformed with these plasmids to yield recombinants.

The *Escherichia coli* JM109 strains respectively transformed with pTEG2, pTEG3 and pTEGP1 are designated as *Escherichia coli* JM109/pTEG2, *Escherichia coli* JM109/pTEG3 and *Escherichia coli* JM109/pTEGP1, respectively. Of these strains, *Escherichia coli* JM109/pTEGP1 has been deposited under accession number FERM BP-5530 at the National Institute of Bioscience and Human-Technology, Agency of Industrial Science and Technology.

Example 3
Expression of Recombinant Endoglycoceramidase II in *Escherichia coli*

*Escherichia coli* JM109/pTEG2, *Escherichia coli* JM109/pTEG3 and *Escherichia coli* JM109/pTEGP1 as obtained in Example 2 were each inoculated to 5 ml of an L medium (0.1% Trypton, 0.05% yeast extract, 0.1% NaCl, pH 7.2) containing 100 µg/ml ampicillin, and subjected to overnight shaking culture at 37° C.; 100 µl of the culture broth was transferred to 120 ml of the same medium. Upon reach of a turbidity (absorbance at 600 nm) of about 0.5 after overnight shaking culture at 37° C., IPTG was added to a final concentration of 1 mM, followed by shaking culture at 37° C. for 4 hours. After completion of the cultivation, the culture broth was centrifuged; cells were collected, suspended in 3 ml of a 10 mM Tris-HCl buffer (pH 8.0) containing 0.5 mM 4-(2-aminoethyl)benzenesulfonyl fluoride hydrochloride, disrupted by ultrasonication, and centrifuged; the resulting supernatant was collected for use as a crude enzyme solution.

The endoglycoceramidase II activity of this crude enzyme solution was determined by the method of Park and Johnson described in The Journal of Biochemistry, 264 (16) 9510–9519 (1989) using purified asialo-GM1 as a substrate. A reaction mixture solution of 50 nmol purified asialo-GM1, 10 µg of bovine serum albumin, an appropriate amount of the enzyme and 0.4% Triton X-100 in 50 µl of a 50 mM sodium acetate buffer (pH 5.5) was incubated at 37° C. for 15 minutes. The reaction was terminated by the addition of 250 µl of a carbonate-cyanide solution (pH 11). The resulting reducing sugar was then quantitated by the method of Park and Johnson [Journal of Biological Chemistry 181, 149–151 (1949)]. For control, the substrate solution was incubated at 37° C. for 15 minutes, after which an alkali solution was added, followed by the addition of the enzyme. One unit of the enzyme is defined as the amount needed to catalyze the hydrolysis of 1 µmol of purified asialo-GM1 per minute under the above-described conditions.

As a result, the activities in these extracts were determined to be about 19 mU/ml for *Escherichia coli* JM109/pTEG2, about 244 mU/ml for *Escherichia coli* JM109/pTEG3 and about 15 mU/ml for *Escherichia coli* JM109/pTEGP1. In other words, it was found that an about 0.5 U of recombinant endoglycoceramidase II can be obtained from 1 liter of *Escherichia coli* JM109/pTEG2 culture broth, about 6.1 U from *Escherichia coli* JM109/pTEG3 culture broth, and about 0.4 U from *Escherichia coli* JM109/pTEGP1 culture broth.

Other modifications of the above described embodiments of the invention which are obvious to those skilled in the art are intended to be within the scope of the following claims.

What is claimed is:

1. An isolated DNA having a sequence encoding a polypeptide possessing endoglycoceramidase activity wherein the isolated DNA comprises a DNA sequence selected from the group consisting of:

(a) a DNA sequence encoding an amino acid sequence of SEQ ID NO:1 or Seg ID NO:3;
   (b) a DNA sequence of SEQ ID NO:2 or SEQ ID NO:4; and
   (c) a DNA sequence which hybridizes to (a) or (b) above.

2. The isolated DNA according to claim 1, wherein the polypeptide is derived from a strain of the genus Rhodococcus.

3. The isolated DNA according to claim 2, wherein the polypeptide is derived from Rhodococcus sp. M-777.

4. A recombinant DNA which comprises the isolated DNA of claim 1.

5. A vector which comprises the recombinant DNA of claim 4.

6. The vector according to claim 5, wherein the recombinant DNA is operably linked to a promoter.

7. A cell of a procaryote or eucaryote transformed with the vector of claim 5.

8. A method for producing a polypeptide possessing endoglycoceramidase activity, comprising the steps of:

(a) culturing the cell of claim 7; and
   (b) recovering the polypeptide possessing endoglycoceramidase activity from the culture obtained in Step (a).

9. A synthetic oligonucleotide probe or primer which specifically hybridizes with the isolated DNA of claim 1.

* * * * *